United States Patent [19]

Lang et al.

[11] Patent Number: 5,131,911
[45] Date of Patent: Jul. 21, 1992

[54] USE OF INDOLE DERIVATIVE FOR DYEING KERATIN MATERIALS, TINCTORIAL COMPOSITIONS, NEW COMPOUNDS AND DYEING PROCESS

[75] Inventors: Gerard Lang, Saint-Gratien; Serge Forestier, Clay-Souilly; Alex Junino, Livry-Gargan; Herve Richard, Paris; Jean Jacques Van den Bossche, Aulnay-sous-Bois, all of France

[73] Assignee: L'Oreal, Paris, France

[21] Appl. No.: 769,811

[22] Filed: Oct. 2, 1991

Related U.S. Application Data

[63] Continuation of Ser. No. 406,289, Sep. 12, 1989, abandoned.

[30] Foreign Application Priority Data

Sep. 12, 1988 [LU] Luxembourg .................. 87338

[51] Int. Cl.$^5$ .............................................. A61K 7/13
[52] U.S. Cl. ........................................ 8/405; 8/406; 8/407; 8/408; 8/410; 8/412; 8/414; 8/423; 8/429; 424/70
[58] Field of Search ............... 8/405, 406, 407, 408, 8/412, 414, 423, 429; 424/70

[56] References Cited

U.S. PATENT DOCUMENTS

| | | | |
|---|---|---|---|
| 3,905,999 | 9/1975 | Krutak | 548/508 |
| 4,208,183 | 6/1980 | Grollier et al. | 8/409 |
| 4,776,857 | 10/1988 | Carroll et al. | 8/423 |
| 4,804,385 | 2/1989 | Grollier et al. | 8/423 |
| 4,808,190 | 2/1989 | Grollier et al. | 8/423 |
| 4,822,375 | 4/1989 | Lang et al. | 8/423 |
| 4,885,006 | 12/1989 | Grollier et al. | 8/423 |
| 4,888,027 | 12/1989 | Grollier et al. | 8/423 |
| 4,932,977 | 6/1990 | Schultz | 8/423 |

FOREIGN PATENT DOCUMENTS 0271186 6/1988 European Pat. Off.
0376776 7/1990 European Pat. Off.

Primary Examiner—A. Lionel Clingman
Assistant Examiner—William S. Parks
Attorney, Agent, or Firm—Cushman, Darby & Cushman

[57] ABSTRACT

Process for dyeing keratin fibers by using derivatives of formula:

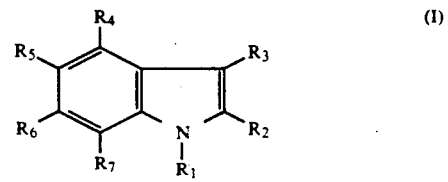

where:
$R_1$ = H, lower alkyl or $SiR_{11}R_{12}R_{13}$;
$R_2$ and $R_3$, which may be identical or different, = H, alkyl, carboxyl, alkoxycarbonyl or —COO-$SiR_{11}R_{12}R_{13}$;
$R_4$ to $R_7$, which may be identical or different, = H or an O—Z group, where Z = H, $C_1$-$C_{20}$alkyl, aralkyl, formyl, $C_2$-$C_{20}$acyl, $C_3$-$C_{20}$alkenyl, —$SiR_{11}R_{12}R_{13}$, —$P(O)(OR_8)_2$, $R_8OSO_2$;
or a heterocycle which may contain a $P(O)(OR_8)$ or $CR_9R_{10}$ group;
with the reservation that at least two of $R_4$ to $R_7$ denotes OZ or form a ring, and that at least one of $R_4$ or $R_7$ represents OZ;
$R_8$ and $R_9$ = H, lower alkyl;
$R_{10}$ = alkoxy, mono- or dialkylamino;
$R_{11}$, $R_{12}$ and $R_{13}$, which may be identical or different, are alkyl groups;
or their alkali metal, alkaline-earth metal, ammonium and amine salts.

30 Claims, No Drawings

USE OF INDOLE DERIVATIVE FOR DYEING KERATIN MATERIALS, TINCTORIAL COMPOSITIONS, NEW COMPOUNDS AND DYEING PROCESS

This is a continuation of application Ser. No. 07/406,289, filed Sept. 12, 1989 now abandoned.

The present invention relates to the use of indole derivatives for dyeing keratin materials, and in particular human hair, to tinctorial compositions using them, to the new compounds derived from indole which are used, as well as to the dyeing processes.

Colorants of the indole family, and in particular 5,6-dihydroxyindole, as well as its derivatives, which are described in French Patent Application 2,595,245, are well known for their use in dyeing keratin fibers.

5,6-Dihydroxyindole leads in particular to black or more or less grey shades.

The Applicants have just discovered that a particular class of indoles which are di- or trisubstituted on the aromatic nucleus and contain at least one substituent in position 4 to 7 allowed the range of hues which could be obtained until the present with these colorants to be enlarged, and more natural hues to be obtained.

The subject of the invention is therefore the use of these particular indoles for dyeing keratin materials, in particular human keratin fibers and notably human hair, and skin or fur.

The tinctorial compositions based on this particular class of indoles are also the subject of the invention.

Another subject of the invention is constituted by the dyeing processes using them.

Finally, the new compounds of the indole family which are used are the subject of the invention.

Other subjects of the invention will appear on reading the description and the examples which follow.

The compounds used according to the invention for dyeing keratin materials, in particular human hair, correspond to the formula:

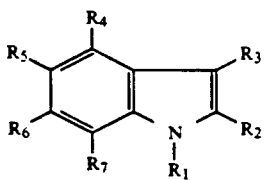

in which:

$R_1$ represents a hydrogen atom or a lower alkyl group or a $SiR_{11}R_{12}R_{13}$ group;

$R_2$ and $R_3$, which may be identical or different, represent a hydrogen atom or an alkyl group, a carboxyl group, a lower alkoxy carbonyl group or a —$COOSiR_{11}R_{12}R_{13}$ group;

$R_4$, $R_5$, $R_6$ and $R_7$, which may be identical or different, represent a hydrogen atom or an O—Z group, Z representing a hydrogen atom or a $C_1$-$C_{20}$ linear or branched alkyl group, an aralkyl group, a formyl group, a $C_2$-$C_{20}$ linear or branched acyl group, a $C_3$-$C_{20}$ linear or branched alkenyl group, a $SiR_{11}R_{12}R_{13}$ group, a —$P(O)(OR_8)_2$ group, on an $R_8OSO_2$— group;

or again $R_4$ and $R_5$, $R_5$ and $R_6$, or $R_6$ and $R_7$, together with the carbon atoms to which they are attached, form a ring optionally containing a carbonyl group, a thiocarbonyl group or a a $>P(O)(OR_8)$ group or a $>CR_9R_{10}$ group with the reservation that at least two of residues $R_4$ to $R_7$ represent an OZ group or form a ring, and that at least one of the radicals $R_4$ or $R_7$ represents an OZ group;

$R_8$ and $R_9$ representing a hydrogen atom or a lower alkyl group, $R_{10}$ representing a lower alkoxy group or a (lower) mono- or dialkylamino group, $R_{11}$, $R_{12}$ and $R_{13}$, which may be identical or different, representing linear or branched lower alkyl groups;

and the corresponding salts of alkali metals, alkaline-earth metals, ammonium and amines.

In the groups defined above, a lower alkyl or lower alkoxy group preferably denotes a group having 1 to 6 carbon atoms, and more particularly the methyl, ethyl and propyl groups for the alkyl groups, and the methoxy and ethoxy groups for the alkoxy group; the ring is preferably a 4- to 6-member ring; the aralkyl group preferably denotes benzyl.

Among the compounds which correspond to formula (I), the following compounds may be mentioned more particularly:

4-hydroxy-5-methoxyindole
6-hydroxy-7-methoxyindole
7-hydroxy-6-methoxyindole
5-ethoxy-4-hydroxyindole
5-ethoxy-4-hydroxy-1-methylindole
7-ethoxy-6-hydroxyindole
4-hydroxy-5-methoxy-2-methylindole
6-hydroxy-7-methoxy-2-methylindole
5-ethoxy-4-hydroxy-2-methylindole
7-ethoxy-6-hydroxy-2-methylindole
5,7-dimethoxy-6-hydroxyindole
5,6,7-trihydroxyindole
indole 4-hydroxy-5-methoxy-2-ethyl carboxylate
indole 6-hydroxy-7-methoxy-2-ethyl carboxylate
indole 7-hydroxy-6-methoxy-2-ethyl carboxylate
indole 4-hydroxy-5-methoxy-2-carboxylic acid
indole 6-hydroxy-7-methoxy-2-carboxylic acid
indole 7-hydroxy-6-methoxy-2-carboxylic acid
indole 5,6,7-trihydroxyindole-2-carboxylic acid
2,3-dimethyl-4-methoxy-7-hydroxyindole
2,3-dimethyl-7-methoxy-4-hydroxyindole.

The tinctorial compositions intended to be used for dyeing keratin materials, and in particular human hair, are essentially characterized in that they contain, in a medium which is appropriate for dyeing these fibers, at least one colorant corresponding to the formula (I) defined above, which is present in sufficient quantities to dye the said keratin materials.

The compounds of formula (I) are preferably present in the composition according to the invention in proportions of between 0.01 and 5% by weight with respect to the total weight of the composition, and preferably between 0.03 and 2.5% by weight.

The compositions which can be used according to the invention can be presented in the form of more or less thickened liquids, creams, foams, gels, oils or powders to be diluted with liquids at the time of use, which are also called poultices.

These compositions can also be presented in devices with one or more compartments or "kits" containing the different components intended to be mixed at the time of use, or again in the form of an aerosol.

When the composition is in a single package, the medium which is appropriate for dyeing is essentially aqueous and has a pH of between 3.5 and 11, and preferably between 5 and 10.5. It is adjusted to the required value with the aid of alkalinizing agents or acidifying agents which are known per se.

A pH-regulating agent having two components which do not inhibit the tinctorial power of the indole colorant can be used. The triethanolamine/tartaric acid and dipotassium hydrogen phosphate/potassium dihydrogen phosphate pairs are preferably used as two-component systems.

These compositions can contain surfactants, present in proportions of between 0.1 and 55% by weight, and preferably between 1 and 40% by weight, with respect to the total weight of the composition.

These aqueous compositions can also contain organic solvents which, when the composition is intended to be used for dyeing human keratin fibers or skin, must be cosmetically acceptable and can be chosen more particularly from the lower $C_1$-$C_4$-alkanols, such as for example ethyl alcohol, propyl or isopropyl alcohol, tert-butyl alcohol, ethylene glycol, propylene glycol, the monomethyl, monoethyl or monobutyl ethers of ethylene, glycol, ethylene glycol monoethyl ether acetate, the monomethyl ethers of propylene glycol and of dipropylene glycol and methyl lactate.

The particularly preferred solvents being ethyl alcohol and ethylene glycol monobutyl ether.

These solvents are preferably used in proportions of from 1 to 60% by weight, and more particularly from 3 to 30% by weight, with respect to the total weight of the composition.

One form of embodiment of the invention can consist in using an anhydrous medium, that is to say containing no more than 1% of water.

Such a composition is intended to be mixed immediately before use with an aqueous cosmetic medium as defined above.

These compositions can also be applied directly onto wetted hair.

The anhydrous medium consists of, according to this variant of the invention, an anhydrous solvent chosen more particularly from the saturated $C_1$-$C_4$-monoalcohols such as ethyl alcohol, isopropyl alcohol, tert-butyl alcohol, the monomethyl, monoethyl or monobutyl ethers of ethylene glycol or ethylene glycol monoethyl ether acetate.

The compositions according to the invention can contain any other additive which is normally used for dyeing keratin materials and in particularly in the case of dyeing human keratin fibers and skin. In the latter case, the additive must be cosmetically acceptable.

They can contain in particularly anionic, nonionic, cationic or amophoteric polymers or their mixtures in proportions of 0.1 to 5% by weight with respect to the total weight of the composition.

These compositions can also be thickened with agents chosen from sodium alginate, gum arabic, guar or carob gum, biopolymers such as xanthan gum, pectins, cellulose derivatives such as methylcellulose, hydroxymethylcellulose, hydroxypropylcellulose or carboxymethylcellulose and the various polymers having thickening functions such as the acrylic acid derivatives. In organic agents such as bentonite can also be used.

These thickeners are present preferably in proportions of between 0.1 and 5% by weight, and in particular between 0.5 and 3% by weight, with respect to the total weight of the composition.

The other additives which can be used in these compositions are chosen in particular from the additives which are normally used in cosmetic compositions such as penetration agents, swelling agents, sequestering agents, antioxidants, buffers, electrolytes, fragrances and the like.

These compositions can also contain other colorants which are normally used for dyeing hair or skin, and more particularly 5,6-dihydroxyindole or its derivatives, described in French Patent Application No. 2,595,245. The tinctorial composition can also contain other colorants, and more particularly precursors of oxidation colorants such as para-phenylenediamines, para-aminophenols, ortho-phenylenediamines, ortho-aminophenols, or ortho-diphenols, as well as couplers such as meta-phenylenediamines, meta-aminophenols, meta-diphenols or pyrazolones, or again autooxidizable rapid oxidation colorants.

These compositions can also contain direct colorants of the family of nitrogen-containing derivatives of the benzene series, anthraquinones, and the like.

The process of dyeing keratin materials and in particular human hair can be implemented in the form of different variants, and more particularly according to the processes described in French Patent Applications FR-A-2,595,245, FR-A-2,593,061, FR-A-2,593,062 and FR-A-2,594,331.

The process for coloring the skin consists in applying on the latter a composition containing a compound of the formula (I), the coloration developing in the oxygen of the air; in certain cases UV radiation allows the appearance of this coloration to be activated.

According to a first variant, an acid or neutral composition containing at least one colorant of the formula (I) can be firstly applied on the keratin material and in particular on hair and furs, and at the end of 5 to 60 minutes of contact is drained and a composition capable of causing oxidation and the development of the colorant is applied. With this objective either an aqueous solution containing an alkalinizing reagent can be used and the coloration will develop simply by means of the oxygen in the air, or an aqueous solution of an oxidizing reagent such as, for example, a peroxide like hydrogen peroxide, an iodate, a periodate or a persulphate can be used.

Another form of implementation consists in adding to the solution which is added secondly, an oxidation catalyst, such as for example, a cobalt, manganese, copper or aluminum salt.

Another variant consists again in applying the composition containing the compounds of formula (I) in an alkaline medium, these compositions containing, for example, ammonia solution or an amine such as monoethanolamine as alkalinizing agent.

After a contact time of 5 to 60 minutes, the keratin materials are rinsed, optionally washed, and dried after rinsing again.

Dyes called "progressive", which consist in superimposing several applications of the composition until a dye is obtained which has a darker hue than the initial hue which the composition allows, can also be carried out by virtue of these compositions.

The formation of the colorant can be accelerated by adding a solution of an oxidizing agent or of an oxidation catalyst either to the keratin material, or into the composition immediately before use. The oxidizing agent can be constituted by hydrogen peroxide, or by a persalt such as sodium perborate, sodium percarbonate, ammonium persulphate or sodium bromate.

When an oxidation catalyst is used, different metal salts such as manganese, cobalt, iron, copper or silver salts can be used.

Manganese sulphate, manganese lactate, cobalt chloride, ferric chloride, copper chloride and ammoniacal silver nitrate may be mentioned as examples.

A third variant of the invention consists in putting the keratin material, and in particular the hair, in contact with a metal salt before or after application of the composition containing the colorant of formula (I); the keratin material is rinsed between the two stages.

This dyeing process can be followed by putting the keratin material in contact with a hydrogen peroxide solution after rinsing, in order optionally to lighten the tint obtained by virtue of the colorant of formula (I).

The metal salts are of the same type as those mentioned above, and more particularly copper or iron, cobalt, manganese or aluminium salts are used, and in a general manner any salt which favors the formation of eumelanines from the colorants of formula (I).

Another variant of the invention consists in applying on the keratin materials a composition (A) containing, in a medium which is appropriate for dyeing, at least one colorant of formula (I) in association with iodide ions, application of composition (A) being preceded or followed by application of a composition (B) which contains, in a medium which is appropriate for dyeing, hydrogen peroxide.

The process in accordance with the invention can also be implemented by applying on the keratin materials at least one composition (A) containing, in a medium which is appropriate for dyeing, at least one colorant of formula (I) in association with hydrogen peroxide having a pH of between 2 and 7, and preferably between 3.5 and 7, application of composition (A) being preceded or followed by application of a composition (B) which contains, in a medium which is appropriate for dyeing, iodide ions.

In these two latter variants of the process according to the invention, the iodide ion is chosen preferably from the alkali metal, alkaline-earth or ammonium iodides, and more particularly potassium iodide.

The process according to the invention can also be implemented using a nitrite as oxidizing agent.

The nitrites which can more particularly be used according to the invention are:
- alkali metal, alkaline-earth or ammonium nitrites or nitrites of any other cation which is cosmetically acceptable when it is used for dyeing living human hair;
- organic nitrite derivatives, such as, for example, amyl nitrite;
- or again nitrite vectors, that is to say compounds which generate a nitrite by conversion.

The particularly preferred nitrites are sodium, potassium or ammonium nitrites.

This process is implemented by applying on the keratin materials the composition based on the colorant of formula (I) defined above (A), followed by application of an aqueous acid composition (B), composition (A) or (B) containing at least one nitrite.

Another embodiment of the invention consists in applying successively on the keratin materials a composition containing, in a medium which is appropriate for dyeing, at a pH of between 2 and 10, an anion of a metal having a good affinity for keratin and having an oxidoreduction potential greater than that of the compounds of formula (I). This anion is chosen preferably from the permanganates or the bichromates, and more particularly potassium permanganate and sodium bichromate. Secondly, a composition containing, in a medium which is appropriate for dyeing, at a pH of between 7 and 10, a colorant of formula (I) defined above is applied.

Finally, in another embodiment of the invention, at least one composition (A) containing, in a medium which is appropriate for dyeing, at least one oxidant chosen from periodic acid, sodium hypochlorite, potassium ferricyanide, silver oxide, Fenton's reagent, lead (IV) oxide and caesium (IV) sulphate is applied on the keratin materials.

Among the compounds used in accordance with the invention for dyeing keratin materials, and in particular human hair or skin, certain are known and others are new.

The new compounds used according to the invention constitute another subject thereof, and they are more particularly chosen from the compounds of formula (I) in which $R_1$, $R_2$, $R_3$, $R_4$, $R_5$, $R_6$ and $R_7$ have the meanings indicated in the table below.

| $R_1$ | $R_2$ | $R_3$ | $R_4$ | $R_5$ | $R_6$ | $R_7$ |
|---|---|---|---|---|---|---|
| H | H | H | OH | $OC_2H_5$ | H | H |
| H | $CH_3$ | H | OH | $OCH_3$ | H | H |
| H | $CH_3$ | H | OH | $OC_2H_5$ | H | H |
| H | H | H | H | $OCH_3$ | OH | $OCH_3$ |
| H | $CH_3$ | $CH_3$ | $OCH_3$ | H | H | OH |
| H | $CH_3$ | $CH_3$ | OH | H | H | $OCH_3$ |
| $CH_3$ | H | H | OH | $OC_2H_5$ | H | H |

The compounds corresponding to general formula (I) can be prepared according to different processes.

A first process consists in carrying out a cyclizing reduction of a dinitrostyrene corresponding to formula (III) according to the following reaction outline:

REACTION OUTLINE A

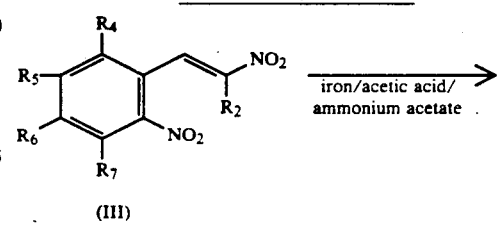

(III)

-continued
REACTION OUTLINE A

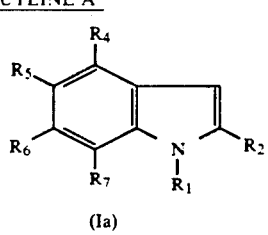
(Ia)

The dinitrostyrene of formula (III) can be prepared by two routes:

a) first route:

REACTION OUTLINE B

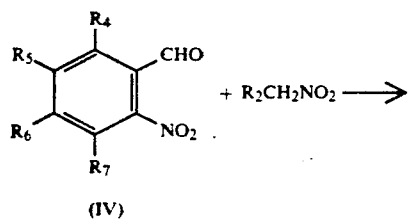
(IV)

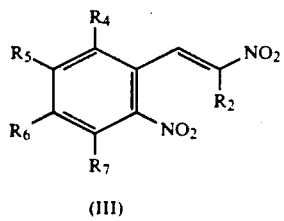
(III)

b) second route:
- first stage:

REACTION OUTLINE C

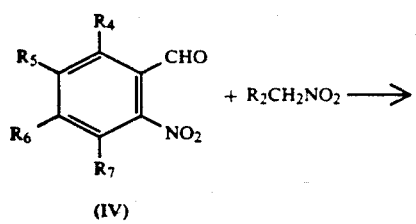
(IV)

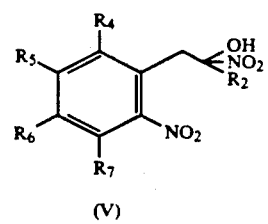
(V)

- second stage:

REACTION OUTLINE D

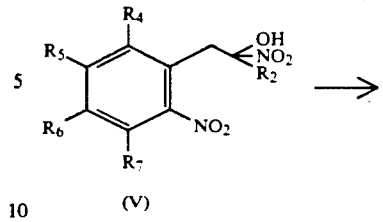
(V)

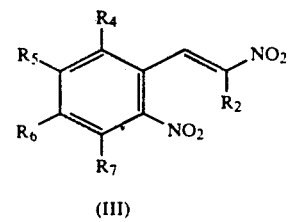
(III)

The aldehyde of formula (IV) can be prepared according to known methods.

This first method is particularly suitable for the preparation of compounds of general formula (I) in which $R_1$ and $R_3$ represent a hydrogen atom, $R_2$ represents a hydrogen atom or an alkyl group and $R_4$, $R_5$, $R_6$ and $R_7$, which may be identical or different, represent a hydrogen atom or an O—Z group in which Z represents a hydrogen atom or an alkyl or aralkyl group.

SECOND METHOD OF PREPARATION a) first route:

REACTION OUTLINE E

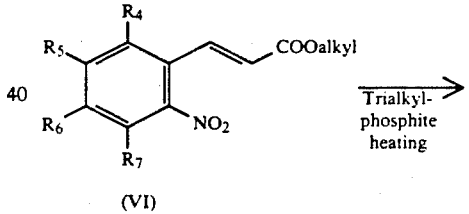
(VI)

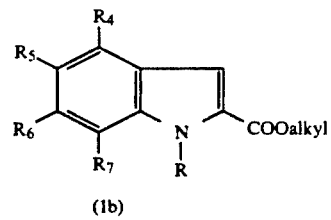
(Ib)

The compound of formula (VI) can be obtained according to the following outline:

REACTION OUTLINE F

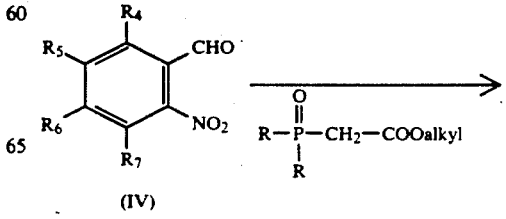
(IV)

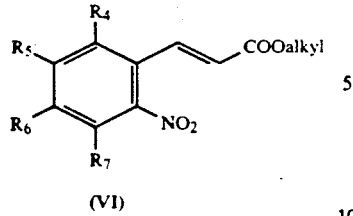

(VI)

b) second route:
Reaction outline G below is used:

REACTION OUTLINE G

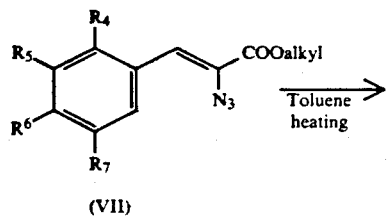

(VII)

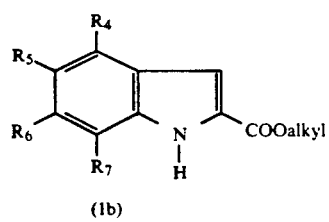

(Ib)

Compound (VII) can be obtained according to the following reaction outline:

REACTION OUTLINE H

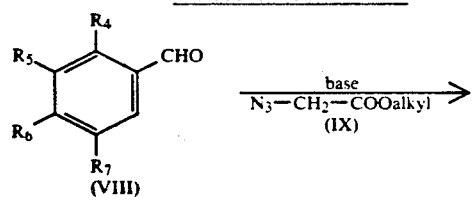

(VIII)

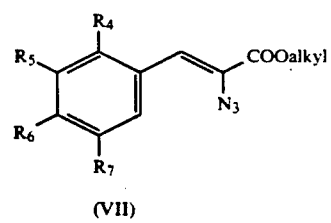

(VII)

The aldehyde of formula (VIII) and the alkyl azidoacetate of formula (IX) can be prepared according to known methods.

c) third route:

REACTION OUTLINE I

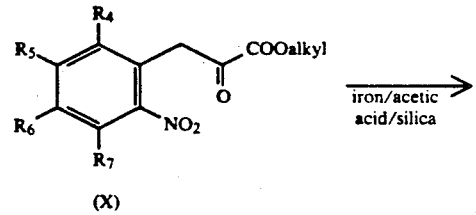

(X)

-continued
REACTION OUTLINE I

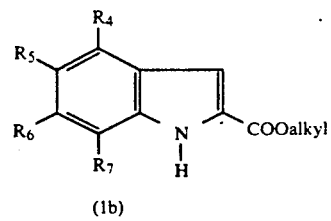

(Ib)

The compound of formula (X) can be prepared according to the following reaction outline:

REACTION OUTLINE J

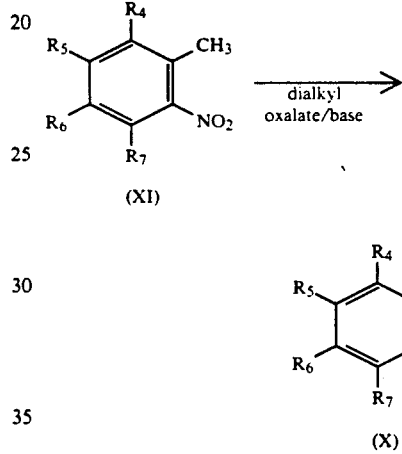

(XI)

(X)

The ortho-nitrotoluene of formula (XI) can be prepared according to known methods.

The compound of formula (Ib) can be converted by hydrolysis to the corresponding carboxylic derivative (Ic) according to reaction outline K.

REACTION OUTLINE K

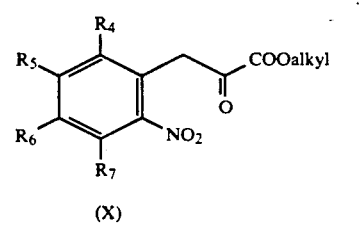

(Ib)

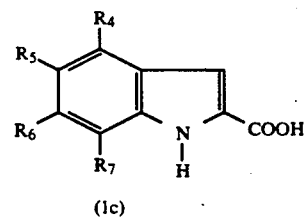

(Ic)

The carboxylic acid (Ic) can be converted to the trialkylsilyl carboxylate (Id) according to reaction outline L.

REACTION OUTLINE L

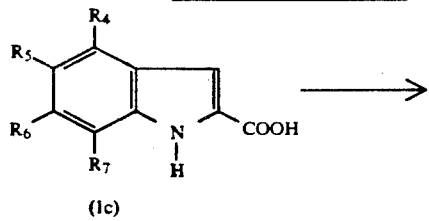

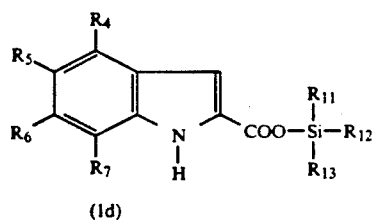

These different routes are well suited for the preparation of the compound of general formula (I) in which $R_1$ and $R_3$ represent a hydrogen atom and $R_2$ represents a carboxyl group, a lower alkoxycarbonyl group or a $COOSiR_{11}R_{12}R_{13}$ group.

THIRD METHOD OF PREPARATION

In the case of compounds of formula (Ie), that is to say when groups $R_2$ and $R_3$ in formula (I) simultaneously represent an alkyl group, the preferred process consists in carrying out the condensation of the 2-bromoalkanone of formula $R_2CHBrCOR_3$, in which $R_2$ and $R_3$ represent alkyl groups, with the aniline of general formula (XII) in which $R_4$, $R_5$, $R_6$ and $R_7$, which may be identical or different, have the meanings indicated above, according to reaction outline M.

REACTION OUTLINE M

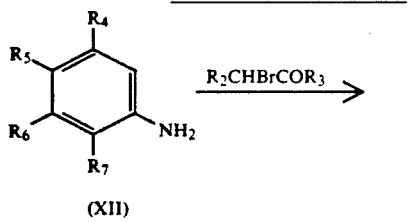

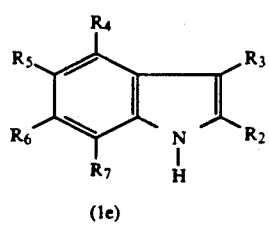

The aniline of formula (XII) is prepared by reduction of the corresponding nitrogen-containing compounds.

FOURTH METHOD OF PREPARATION

Compounds (If), corresponding to formula (I) in which $R_1$ is an alkyl group, can be prepared by alkylation of compounds (Ia) to (Ie).

FIFTH METHOD OF PREPARATION

Compounds of formula (Ia) to (If), obtained according to the processes described above and in which at least one of groups $R_4$ to $R_7$ represent an O—Z group, Z representing an aralkyl group, can be subjected to a hydrogenolysis reaction to lead to compounds of general formula (I) in which at least one of the substituents $R_4$ to $R_7$ represents an OH group.

The following examples are intended to illustrate the preparation of certain of the compounds according to the invention.

PREPARATION EXAMPLE 1

Preparation of 5-ethoxy-4-hydroxyindole a/ Preparation of 2-benzyloxy-3-ethoxy-6-nitrobenzaldehyde 3-Ethoxysalicylaldehyde (498 g, 3 moles) and sodium hydroxide (140 g, 3.5 moles) in 1.5 liters of water are introduced into a 4 liter reactor provided with mechanical stirring, a condenser and a nitrogen inlet. The mixture is taken to 60° C. and benzenesulphonyl chloride is added dropwise over three-quarters of an hour. The mixture is heated to 75° C. for a quarter of an hour. It is cooled. An oil forms which crystallizes with time. It is filtered, washed with water and dried. The 2-hydroxy-3-ethoxybenzaldehyde benzenesulphonate (901 g, yield=98%) is used for the following stage. It can be recrystallized from 90:10 acetic acid/water. A white powder is obtained, m.p.=68°-69° C.

The above derivative (800 g) is introduced into 1 liter of fuming nitric acid (d=1.52) cooled to −20° C. by means of a dry ice/ethanol bath, over 30 minutes with vigorous stirring. The mixture is left at 0° C. for 10 minutes and then poured into 3 liters of iced water. A yellow oil separates.

This oil is dissolved in 1.5 liters of methanol to which is added, at 50°-60° C., a solution of caustic soda (100 g) in 130 cm³ of water and 300 cm³ of methanol. The orangish-yellow phenate obtained is filtered off and washed with 2 times 100 cm³ of methanol.

This filtercake is taken up in 1.3 liters of water, heated to 80° C. and acidified with 250 cm³ of 6N hydrochloric acid. The precipitate is filtered off, washed with water and dried. After drying a pale yellow precipitate of 3-ethoxy-2-hydroxy-6-nitrobenzaldehyde (162 g, yield=32% with respect to the starting 3-ethoxysalicylaldehyde, m.p.=77°-78° C.) is obtained.

A mixture of 3-ethoxy-2-hydroxy-6-nitrobenzaldehyde (58 g, 0.275 mole), benzyl chloride (34.8 cm³, 0.302 mole) and potassium carbonate (41.6 g, 0.302 mole) in 300 cm³ of dimethylformamide is heated for 3 hours under reflux with stirring. The reaction mixture is poured into 1 liter of iced water and the precipitate is filtered off. It is washed with water and dried. A light beige powder of 2-benzyloxy-3-ethoxy-2-nitrobenzaldehyde (72 g, yield=86%, m.p.=110°-111° C.) is obtained.

b/ Preparation of 2-benzyloxy-3-ethoxy-6,β-dinitrostyrene

Potassium hydroxide (34 g) in 60 cm³ of water and 500 cm³ of ethanol are added over 30 minutes to a mixture of the above derivative (70 g, 0.232 mole) and nitromethane (20.3 g, 0.33 mole) in absolute ethanol (800 cm³) under nitrogen and at −15° C. The mixture is left at −10° C. for 2 hours with vigorous stirring. Concentrated hydrochloric acid is added to this heterogeneous mixture at a temperature lower than 0° C. After addition of water the precipitate is filtered off, washed with water and dried. A light beige precipitate (81 g, yield=96%) is obtained.

This precipitate is heated to 100° C. with 400 cm³ of acetic anhydride and 120 g of anhydrous sodium acetate for 10 minutes. The mixture is cooled and poured into iced water. 2-Benzyloxy-3-ethoxy-6,β-dinitrostyrene (62 g, yield=83%, m.p.=110° C.) is obtained.

c/ Preparation of 4-benzyloxy-5-ethoxyindole

The above derivative (60 g, 0.174 mole) is added in portions over 20 minutes to a mixture of activated iron powder (240 g), anhydrous ammonium acetate (134 g) absolute ethanol (800 cm³) and glacial acetic acid (500 cm³) under nitrogen, with stirring and at 65° C., keeping the temperature below 85° C. The mixture is left at this temperature for 5 minutes, cooled to around 50° C. and the ferric sludge is filtered off hot. The filtercake is rinsed with 200 cm³ is hot ethanol. The filtrate is poured into water and the precipitate formed is filtered off, washed with water and dried. It is taken up in dichloromethane, treated with animal charcoal and filtered on a bed of silica 60. After evaporation of the solvent and drying, 4-benzyloxy-5-ethoxyindole (22 g, yield=47%, m.p.=122°-123° C.) is obtained.

Analysis: $C_{17}H_{17}NO_2$
Calculated: C 76.38; H 6.41; N 5.24
Found: C 76.25; H 6.44; N 5.30 d/ Preparation of 5-ethoxy-4-hydroxyindole

The above derivative (22.6 g) is added over 15 minutes to a mixture of absolute ethanol (180 cm³), cyclohexane (25 cm³) and 10% palladium-on-charcoal (3.76 g) heated to 60° C. The mixture is left under reflux for 1 hour 30 minutes. It is filtered hot, evaporated to dryness and taken up in diisopropyl ether. The solution is dried, concentrated to a third and left to precipitate. 5-Ethoxy-4-hydroxyindole (14.4 g, yield=96%, m.p.=120°-1° C.) is recovered.

Analysis: $C_{10}H_{11}NO_2$
Calculated: C 67.78; H 6.26; N 7.90
Found: C 67.72; H 6.28; N 7.98

PREPARATION EXAMPLE 2

Preparation of 5-ethoxy-4-hydroxy-2methylindole a/ Preparation of 2-benzyloxy-3-ethoxy-6,β-dinitromethylstyrene Nitroethane (28.7 cm³, 0.4 mole) is added dropwise to a mixture of 2-benzyloxy-3-ethoxy-6-nitrobenzaldehyde (60 g, 0.2 mole) obtained in Example 1a, in glacial acetic acid (300 cm³) and dry ammonium acetate (30.8 g, 0.4 mole) at 60° C. over 30 minutes. After refluxing for 5 hours, the reaction mixture is poured into 800 cm³ of iced water. The brown precipitate obtained is filtered off and recrystallized from ethanol. 2-Benzyloxy-3-ethoxy-6,β-dinitromethylstyrene is obtained in the form of a yellow powder (24 g, yield=35%, m.p.=89°-90° C.).

b/ Preparation of 4-benzyloxy-5-ethoxy-2-methylindole

A suspension of ammonium acetate (47 g) in 400 cm³ of absolute ethanol and 200 cm³ of acetic acid is taken to 60° C. Activated iron (66 g) is added to this solution; the mixture is taken to 80°-85° C. and the above derivative (22 g, 0.061 mole) is added over 30 minutes with vigorous stirring. After stirring for 30 minutes at 80° C., the ferric sludge is filtered off and washed with 200 cm³ of absolute ethanol. The filtrate is diluted with ice. The precipitate formed is filtered off, washed with water and dried. After passage through a silica 60 column (eluant: 65:35 $CH_2Cl_2$/toluene) 4-benzyloxy-5-ethoxy-2-methylindole (5.1 g, yield=30%, m.p.=67°-8° C.) is recovered.

Analysis: $C_{18}H_{19}NO_2$
Calculated: C 76.84; H 6.81; N 4.98
Found: C 77.01; H 6.78; N 4.86 c/ Preparation of 5-ethoxy-4-hydroxy-2-methylindole

The above derivative (5 g, 0.0177 mole) is added by fractions over 15 minutes to a mixture of absolute ethanol (50 cm³) cyclohexane (8 cm³) and 10% palladium-on-charcoal (1 g) heated to 60° C. The mixture is heated under reflux for 3 hours, cooled and filtered. The solution is evaporated to dryness and taken up in diisopropyl ether. The ethereal phase is concentrated and cooled. A solid is obtained which is filtered off and dried to give 5-ethoxy-4-hydroxy-2-methylindole (3.2 g, yield=94%, m.p.=77°-8° C.).

Analysis: $C_{11}H_{13}NO_2$
Calculated: C 69.09; H 6.85; N 7.32
Found: C 68.84; H 6.83; N 7.19

PREPARATION EXAMPLE 3

Preparation of 4-hydroxy-5-methoxyindole a/ Preparation of 2-benzyloxy-3-methoxy-6,β-dinitrostyrene This compound is obtained according to the operating method described in Example 1b, in which the 2-benzyloxy-3-ethoxy-6-nitrobenzaldehyde is replaced with 2-benzyloxy-3-methoxy-6-nitrobenzaldehyde. A pale yellow powder (yield=83%, m.p.=118°-119° C.) is obtained.

b/ Preparation of 4-benzyloxy-5-methoxyindole

This compound is obtained according to the operating method described in Example 1c, in which the 2-benzyloxy-3-epoxy-6,β-dinitrostyrene is replaced with 2-benzyloxy-3-methoxy-6,β-dinitrostyrene. A white powder (yield=86%, m.p.=83°-84° C.) is obtained.

Analysis: $C_{16}H_{15}NO_2$
Calculated: C 75.87; H 5,97; N 5.53
Found: C 75.88; H 6.03; N 5.48 c/ Preparation of 4-hydroxy-5-methoxyindole

This compound is obtained according to the operating method described in Example 1d, in which the 4-benzyloxy-5-ethoxyindole is replaced with 4-benzyloxy-5-methoxyindole. A white powder (yield=90%, m.p.=146° C., decomposition) is obtained.

Analysis: $C_9H_9NO_2$
Calculated: C 66.25; H 5.56; N 8.58
Found: C 66.34; H 5.59; N 8.57

PREPARATION EXAMPLE 4

Preparation of 4-hydroxy-5-methoxy-2-methylindole a/ Preparation of 2-benzyloxy-3-methoxy-6,β-dinitromethylstyrene This compound is obtained according to the operating method described in Example 2a, in which the 2-benzyloxy-3-ethoxy-6-nitrobenzaldehyde is replaced with 2-benzyloxy-3-methoxy-6-nitrobenzaldehyde. A light yellow powder (yield=53%, m.p.=149°-150° C.) is obtained.

b/ Preparation of 4-benzyloxy-5-methoxy-2-methylindole

This compound is obtained according to the operating method described in Example 2b, in which the 2-benzyloxy-3-ethoxy-6,β-dinitromethylstyrene is replaced with 2-benzyloxy-3-methoxy-6,β-dinitromethylstyrene. A pale yellow powder (yield=40%, m.p.=74°-75° C.) is obtained.

Analysis: $C_{17}H_{17}NO_2$
Calculated: C 76.38; H 6.41; N 5.24
Found: C 76.36; H 6.44; N 5.20 c/ Preparation of 4-hydroxy-5-methoxy-2-methylindole

This compound is obtained according to the operating method described in Example 2c, in which the 4-benzyloxy-5-ethoxy-2-methylindole is replaced by 4-benzyloxy-5-methoxy-2-methylindole. Following the operating method of Example 2 a pale yellow powder is obtained (yield=89%, m.p.=118°-119° C.).

Analysis: $C_{10}H_{11}NO_2$
Calculated: C 67.78; H 6.26; N 7.90
Found: C 67.71; H 6.32; N 7.90

PREPARATION EXAMPLE 5

Preparation of 6-hydroxy-7-methoxyindole a/ Preparation of 6-benzyloxy-7-methoxyindole This compound is obtained according to the operating method described in Example 1c, in which the 2-benzyloxy-3-ethoxy-6,β-dinitrostyrene is replaced with 4-benzyloxy-3-methoxy-2,β-dinitrostyrene. White crystals (yield=75%, m.p.=66°-67° C.) are obtained.

Analysis: $C_{16}H_{15}NO_2$
Calculated: C 75.87; H 5.97; N 5.53
Found: C 75.74; H 6.00; N 5.34 b/ Preparation of 6-hydroxy-7-methoxyindole

This compound is obtained according to the operating method described in Example 1d, in which the 4-benzyloxy-5-ethoxyindole is replaced by 6-benzyloxy-7-methoxyindole. A white powder is obtained (yield: 86%, m.p.=83°-84° C.).

Analysis: $C_9H_9NO_2$
Calculated: C 66.25; H 5.56; N 8.58
Found: C 66.28; H 5.67; N 8.57

PREPARATION EXAMPLE 6

Preparation of 5,7-dimethoxy-6-hydroxyindole a/ Preparation of 4-acetoxy-1-diacetoxymethyl-3,5-dimethoxybenzene A suspension of 25 g (0.137 mole) of 3,5-dimethoxy-4-hydroxybenzaldehyde in 60 cm³ of acetic anhydride is cooled to about 5° C. 0.2 cm³ of perchloric acid is added dropwise. The reaction mixture gains in mass and then becomes fluid. It is stirred for one hour and then poured into iced water. After stirring for 30 minutes, it is filtered, washed with water and then 96% alcohol and dried under vacuum. 40.1 g of the desired product are obtained in the form of white crystals (yield=93%).

b/ Preparation of 4-acetoxy-1-diacetoxymethyl-3,5-dimethoxy-2-nitrobenzene 32 cm³ of 100% nitric acid are cooled to −30° C. 100 cm³ of acetic anhydride then 40 g (0.123 mole) of 4-acetoxy-1-diacetoxymethyl-3,5-dimethoxybenzene are added with stirring. The temperature is left to increase to about −15° C. After stirring at this temperature for 30 minutes, the reaction mixture is poured into iced water. After filtration, washing with water and drying under vacuum, 43.8 g of the desired product are obtained in the form of a slightly yellow powder (yield=96%).

c/ Preparation of 3,5-dimethoxy-4-hydroxy-2-nitrobenzaldehyde

A suspension of 43 g (0.116 mole) of 4-acetoxy-1-diacetoxymethyl-3,5-dimethoxy-2-nitrobenzene in 500 cm³ of 2N hydrochloric acid is heated under reflux for 2 hours. The reaction mixture is left to return to ambient temperature, then the precipitate formed is filtered off. After washing with water and drying under vacuum, 25.8 g of the desired product is obtained in the form of a slightly yellow solid (yield=98%).

d/ Preparation of 3,5-dimethoxy-4-hydroxy-2,β-dinitrostyrene

A suspension of 20 g (0.088 mole) of 3,5-dimethoxy-4-hydroxy-2-nitrobenzaldehyde and 21 g (0.27 mole) of dry ammonium acetate in 400 cm³ of acetic anhydride and 15.8 g (0.26 mole) of nitromethane is heated under reflux for 2 hours. The reaction mixture is cooled, then the precipitate is filtered off. After washing with water, recrystallization from an ethanol-water mixture and drying under vacuum, 13.9 g of the desired product is obtained in the form of orangish-yellow crystals (yield=58%).

e/ Preparation of 5,7-dimethoxy-6-hydroxyindole

A mixture of 10 g (0.037 mole) of 3,5-dimethoxy-4-hydroxy-2,β-dinitrostyrene and 10 g of palladium hydroxide on charcoal in 400 cm³ of ethanol and 7 cm³ of formic acid is heated under reflux for 3 hours. After cooling, the reaction mixture is filtered through Celite. The filtrate is evaporated to dryness. The residue is redissolved in dichloromethane and the solution is filtered on silica gel. After distillation of the solvent under reduced pressure and recrystallization from diisopropyl ether, 1 g of the desired product is obtained in the form of a whitish solid (yield=14%).

Analysis: $C_{10}H_{11}NO_3$
Calculated (0.5 $H_2O$): C 59.40; H 5.94; N 6.93
Found: C 59.32; H 5.78; N 7.20

PREPARATION EXAMPLE 7

Preparation of 2,3-dimethyl-4-hydroxy-7-methoxyindole a/ Preparation of 3-benzyloxy-6-methoxyaniline 1.38 kg of zinc powder and 15 g of ammonium chloride in 3.25 liters of ethanol to which have been added 600 ml of water are heated to 80° C. 2.5 mole (648 g) of 3-benzyloxy-6-methoxynitrobenzene is added little by little. Stirring is continued for 15 minutes after the end of the addition. The zinc is removed by filtering the reaction medium hot. The product crystallizes from the filtrate by cooling. After centrifuging and then washing with petrol ether, the product is dried. It melts at 81° C.

Analysis of the product obtained give the following results.

Analysis: $C_{14}H_{15}NO_2$
Calculated: C 73.36; H 6.55; N 6.11; O 13.97
Found: C 73.38; H 6.51; N 6.02; O 14.02 b/ Preparation of 4-benzyloxy-2,3-dimethyl-7-methoxyindole 1 mole (229 g) of 3-benzyloxy-6-methoxyaniline is added to 700 ml of dimethylformamide and 0.5 mole (76 g) of 2-bromobutanone. The reaction medium is heated to 40° C. for 2 hours 30 minutes and then to 120° C. for three quarters of an hour. By adding ice and then cooling, an oil is obtained which is decanted and then dissolved in ethyl acetate. After washing with a 2N solution of hydrochloric acid, then with water and evaporation of the ethyl acetate, the desired product is obtained in the form of a dry extract which is recrystallized from cyclohexane under reflux. The desired product melts at 100° C.

Analysis of the product obtained gives the following results.

Analysis: $C_{18}H_{19}NO_2$
Calculated: C 76.87; H 6.76; N 4.98; O 11.39
Found: C 76.94; H 6.72; N 5.04; O 10.41 c/ Preparation of 2,3-dimethyl-4-hydroxy-7-methoxyindole 0.14 mole (39.5 g) of 4-benzyloxy-2,3-dimethyl-7-methoxyindole and 4 g of 10% palladium-on-charcoal in 120 ml of 96° ethanol to which have been added 80 ml of cyclohexane is heated under reflux. After 1 hour 30 minutes the catalyst is removed by hot filtration. The desired product is obtained by concentrating the filtrate to dryness. It is purified by dissolving it hot in isopropyl ether, filtering in the presence of charcoal and evaporating the filtrate to dryness. It melts at 164° C.

Analysis of the product obtained gives the following results.

Analysis: $C_{11}H_{13}NO_2$
Calculated: C 69.11; H 6.81; N 7.33; O 16.75
Found: C 69.12; H 6.86; N 7.31; O 16.93

PREPARATION EXAMPLE 8

Preparation of 2,3-dimethyl-7-hydroxy-4-methoxyindole a/ Preparation of 6-benzyloxy-3-methoxyaniline 6-Benzyloxy-3-methoxyaniline is obtained from 6-benzyloxy-3-methoxynitrobenzene according to the operating method described for the preparation of 3-benzyloxy-6-methoxyaniline (Example 7a). The product is recrystallized from 96° ethanol. It melts at 48° C.

Analysis of the product obtained gives the following results.

Analysis: $C_{14}H_{15}NO_2$
Calculated: C 73.33; H 6.55; N 6.11; O 13.97
Found: C 73.29; H 6.49; N 6.15; O 13.98 b/ Preparation of 7-benzyloxy-2,3-dimethyl-4-methoxyindole

7-Benzyloxy-2,3-dimethyl-4-methoxyindole is prepared from 6-benzyloxy-3-methoxyaniline according to the operating method described for the preparation of 4-benzyloxy-2,3-dimethyl-7-methoxyindole (Example 7b). The product obtained melts at 76° C.

Analysis of the product obtained gives the following results.

Analysis: $C_{18}H_{19}NO_2$
Calculated: C 76.87; H 6.76; N 4.98; O 11.39
Found: C 76.90; H 6.77; N 4.97; O 11.54 c/ Preparation of 2,3-dimethyl-7-hydroxy-4-methoxyindole 2,3-Dimethyl-7-hydroxy-4-methoxyindole is prepared from 7-benzyloxy-2,3-dimethyl-4-methoxyindole according to the operating method described for the preparation of 2,3-dimethyl-4-hydroxy-7-methoxyindole (Example 7c). It melts at 159° C.

Analysis of the product obtained gives the following results.

Analysis: $C_{11}H_{13}NO_2$
Calculated: C 69.11; H 6.81; N 7.33; O 16.75
Found: C 69.14; H 6.82; N 7.37; O 16.81

PREPARATION EXAMPLE 9

Preparation of 5-ethoxy-4-hydroxy-1-methylindole a/ Preparation of 4-benzyloxy-5-ethoxy-1-methylindole The 4-benzyloxy-5-ethoxyindole (1.8 g, 0.0067 mole) obtained in Example (1c), 50% caustic soda (8 ml), toluene (5.4 ml) and tetrabutylammonium hydrogen sulphate (180 mg) are successively introduced. The mixture is heated to 60° C. and dimethyl sulphate (1 g) is introduced. The mixture is left at 60° C. for 30 minutes, diluted with water and the two phases are separated. The organic phase is washed with water, dried and the solvent evaporated. A colorless oil of 4-benzyloxy-5-ethoxy-1-methylindole (1.6 g; yield = 95%) is obtained.

Analysis of the product obtained gives the following results.

Analysis: $C_{18}H_{19}NO_2$
Calculated: C 76.84; H 6.81; N 4.98
Found: C 76.82; H 6.79; N 4.88 p/ Preparation of 5-ethoxy-4-hydroxy-1-methylindole

A mixture of the above derivative (1.5 g, 0.0053 mole), cyclohexane (3 ml), absolute ethanol (25 ml) and palladium-on-charcoal (0.3 g) is heated under reflux for 2 hours. The mixture is filtered hot and the solvent evaporated. A light yellow powder of 5-ethoxy-4-hydroxy-1-methylindole (0.9 g; yield = 88%; m.p. = 69°–70° C.) is obtained.

Analysis of the product obtained gives the following results.

Analysis: $C_{11}H_{13}NO_2$
Calculated: C 69.09; H 6.85; N 7.32
Found: C 69.06; H 6.88; N 7.40

The following examples are intended to illustrate the use of compounds of formula (I) in dyeing keratin fibers.

EXAMPLE 1

Hair containing 90% white hair is colored by successively applying two compositions with an intermediate rinse.

The hair is impregnated for 15 minutes with the gel of composition (A) which follows:

5-ethoxy-4-hydroxy-2-methylindole: 0.5 g
potassium iodide: 0.5 g
ethyl alcohol: 10.0 g
hydroxypropylguar sold under the name Jaguar HP 60 by the Meyhall company: 1.0 g
glycoside alkyl ether sold at a concentration of 60% AS under the name Triton CG 110 by the Seppic company: 5.0 g AS
spontaneous pH: 6.5
water: qs 100.0 g The hair is drained and rinsed with water, then a 12.5 volume hydrogen peroxide solution at a pH of 3 is applied, massaging the hair for 5 minutes.

After rinsing with water and drying, a light matt ash-blond color is obtained.

EXAMPLE 2

Hair containing 90% white hair is colored by applying the following composition for 15 minutes:
4-hydroxy-5-methoxy-2-methylindole: 0.62 g
ethylene glycol monobutyl ether: 10.0 g
triethanolamine: qs pH 8 water: qs 100.0 g

After rinsing with water and drying, a medium pearly grey-beige is obtained which is reinforced with further applications. Thus, a fairly intense mauve ash-blond is obtained on the second application.

EXAMPLE 3

Hair containing 90% white hair is colored by successively applying two compositions with an intermediate rinse.

The air is impregnated for 5 minutes with the following compositions:
- copper sulphate with 5 molecules of water: 1.0 g
- sodium lauryl ether sulphate ethoxylated with 2 moles of ethylene oxide: 0.3 g AS
- very high molecular weight carboxyvinyl polymer sold under the name Carbopol 934 by the Goodrich Chemical company: 0.5 g AS
- monoethanolamine: qs pH 9.5
- water: qs 100.0 g The hair is drained and rinsed with water, then the following composition is applied for 5 minutes:
- 6-hydroxy-7-methoxyindole: 0.83 g
- ethylene glycol monobutyl ether: 16.7 g
- triethanolamine: qs pH 8.7
- water: qs 100.0 g After rinsing with water and drying, a matt ash-blond color is obtained.

EXAMPLE 4

Hair containing 90% white hair is colored by successively applying two compositions with an intermediate rinse.

The hair is impregnated for 15 minutes with the gel of composition (A) which follows:
- 4-hydroxy-5-ethoxyindole: 1.0 g
- potassium iodide: 1.0 g
- ethyl alcohol: 10.0 g
- hydroxypropylguar sold under the name Jaguar HP 60 by the Meyhall company: 1.0 g
- glycoside alkyl ether sold at a concentration of 60% AS under the name Triton CG 110 by the Seppic company: 5.0 g AS
- spontaneous pH: 6.4
- water: qs 100.0 g The hair is drained and rinsed with water, then a 12.5 volume solution of hydrogen peroxide at a pH of 3 is applied, massaging the hair for 5 minutes.

After rinsing with water, a purple color of medium intensity is obtained.

On permanent-waved hair containing 90% white hair a more powerful purple color is obtained.

EXAMPLE 5

Hair containing 90% white hair is colored by successively applying two compositions with an intermediate rinse.

The hair is impregnated for 5 minutes with the following composition:
- copper sulphate with 5 molecules of water: 0.25 g
- sodium lauryl ether sulphate ethoxylated with 2 moles of ethylene oxide: 0.3 g AS
- very high molecular weight carboxyvinyl polymer sold under the name Carbopol 934 by the Goodrich Chemical company: 0.5 g AS
- monoethanolamine: qs pH 9.5
- water: qs 100.0 g The hair is drained and rinsed with water and then the following composition is applied for 5 minutes:
- 4-hydroxy-5-methoxyindole: 0.62 g
- ethylene glycol monobutyl ether: 10.0 g
- triethanolamine: qs pH 8
- water: qs 100.0 g After rinsing with water and drying an intense mauve color is obtained.

EXAMPLE 6

Permanent-waved hair containing 90% white hair is colored by applying the following composition for 20 minutes:
- 4-hydroxy-5-methoxy-2-methylindole: 0.5 g
- ethylene glycol monobutyl ether: 25.0 g
- monoethanolamine: qs pH 10.2
- water: qs 100.0 g After rinsing with water and drying, a pearly ash-blond color is obtained which is reinforced with further applications.

EXAMPLE 7

Hair containing 90% white hair is colored by successively applying two compositions with an intermediate rinse.

The hair is impregnated for 15 minutes with the gel of composition (A) which follows:
- 4-hydroxy-5-methoxyindole: 0.5 g
- potassium iodide: 0.5 g
- ethyl alcohol: 10.0 g
- hydroxypropylguar sold under the name Jaguar HP 60 by the Meyhall company: 1.0 g
- glycoside alkyl ether sold at a concentration of 60% AS under the name Triton CG 110 by the Seppic company: 5.0 g AS
- spontaneous pH: 6.7
- water: qs 100.0 g The hair is drained and rinsed with water, then a 12.5 volume hydrogen peroxide solution at a pH of 3 is applied, massaging the hair, for 5 minutes.

After rinsing with water and drying, a powerful purple color is obtained.

At a pH which is controlled at a value of 8.5 with triethanolamine, the color is a slightly lighter purple then at the spontaneous pH.

EXAMPLE 8

Permanent-waved hair containing 90% white hair is colored by successively applying two compositions with an intermediate rinse.

The hair is impregnated for 15 minutes with the solution of composition (A) which follows:
- 6-hydroxy-7-methoxyindole: 1.0 g
- potassium iodide: 1.0 g
- ethyl alcohol: 10.0 g
- nonylphenol ethoxylated with 9 moles of ethylene oxide sold by the Henkel company under the name Sinnopal NP 9: 10.0 g
- citric acid: qs pH 4
- water: qs 100.0 g The hair is drained and rinsed with water, then a 12.5 volume solution of hydrogen peroxide at a pH of 3 is applied, massaging the hair, for 5 minutes.

After rinsing with water and drying a light golden coppery blond color is obtained.

EXAMPLE 9

Hair containing 90% white hair is colored by successively applying two composition with an intermediate rinse.

The hair is impregnated for 5 minutes with the following composition:
- copper sulphate with 5 molecules of water: 1.0 g
- sodium lauryl ether sulphate ethoxylated with 2 moles of ethylene oxide: 0.3 g AS
- very high molecular weight carboxyvinyl polymer sold under the name Carbopol 934 by the Goodrich Chemical company: 0.5 g AS
- monoethanolamine: qs pH 9.5
- water: qs 100.0 g The hair is drained and rinsed with water, then the following composition is applied for 5 minutes:
- 4-hydroxy-5-methoxy-2-methylindole: 0.5 g
- ethylene glycol monobutyl ether: 25.0 g
- monoethanolamine: qs pH 10.2
- water: qs 100.0 g After rinsing with water and drying. an intense blue ash-blond color is obtained.

EXAMPLE 10

Permanent-waved hair containing 90% white hair is colored by successively applying two compositions with an intermediate rinse.

The hair is impregnated for 15 minutes with the gel of composition (A) following:
- 4-hydroxy-5methoxyindole: 0.5 g
- 5,6-dihydroxyindole: 0.3 g
- potassium iodide: 0.5 g
- ethyl alcohol: 10.0 g
- hydroxypropylguar sold under the name Jaguar HP 60 by the Meyhall company: 1.0 g
- glycoside alkyl ether sold at a concentration of 60% AS under the name Triton CG 110 by the Seppic company: 5.0 g AS
- spontaneous pH: 6.7
- water: qs 100.0 g The hair is drained and rinsed with water, then a 12.5 volume solution of hydrogen peroxide at a pH of 3 is applied, massing the hair, for 5 minutes.

After rinsing with water and drying, a violet-black color is obtained.

EXAMPLE 11

Hair containing 90% white hair is colored by successively applying two compositions with an intermediate rinse.

The hair is impregnated for 5 minutes with the following composition:
- copper sulphate with 5 molecules of water: 1.0 g
- sodium lauryl ether sulphate ethoxylated with 2 moles of ethylene oxide: 0.3 g AS
- very high molecular weight carboxyvinyl polymer sold under the name of Carbopol 934 by the Goodrich Chemical company: 0.5 g AS
- monoethanolamine: qs pH 9.5
- water: qs 100.0 g The hair is drained and rinsed with water, then the following composition is applied for 5 minutes:
- 2,3-dimethyl-7-hydroxy-4-methoxyindole: 1.0 g
- ethylene glycol monobutyl ether: 25.0 g
- triethanolamine: qs pH 8.7
- water: qs 100.0 g After rinsing with water and drying, a pearly mahogany blond is obtained.

EXAMPLE 12

Permanent-waved hair containing 90% white hair is colored by applying the following composition for 20 minutes:
- 2,3-dimethyl-4-hydroxy-7-methoxyindole: 1.0 g
- ethylene glycol monobutyl ether: 25.0 g
- triethanolamine: qs pH 8.5
- water: qs 100.0 g After rinsing with water and drying, a very light beige color is obtained which is reinforced in a very progressive manner with further applications.

EXAMPLE 13

Permanent-waved hair containing 90% white hair is colored by successively applying two compositions with an intermediate rinse.

The hair is impregnated for 15 minutes with the gel of composition (A) following:
- 2.3-dimethyl-7-hydroxy-4-methoxyindole: 0.25 g
- potassium iodide: 0.25 g
- ethyl alcohol: 10.0 g
- hydroxypropylguar sold under the name Jaguar HP 60 by the Meyhall company: 1.0 g
- glycoside alkyl ether sold at a concentration of 60% AS under the name Triton CG 110 by the Seppic company: 5.0 g AS
- spontaneous pH: 6.8
- water: qs 100.0 g The hair is drained and rinsed with water then a 12.5 volume solution of hydrogen peroxide at a pH of 3 is applied, massaging the hair, for 5 minutes.

After rinsing with water and drying, a light pearly blond colored is obtained.

EXAMPLE 14

Hair containing 90% white hair is colored by successively applying two compositions with an intermediate rinse.

The hair is impregnated for 5 minutes with the following composition:
- copper sulphate with 5 molecules of water: 1.0 g
- sodium lauryl ether sulphate ethoxylated with 2 moles of ether oxide: 0.3 g AS
- very high molecular weight carboxyvinyl polymer sold under the name Carbopol 934 by the Goodrich Chemical company: 0.5 g AS
- monoethanolamine: qs pH 9.5
- water: qs 100.0 g The hair is drained and rinsed with water then the following composition is applied for 5 minutes:
- 2,3-dimethyl-4-hydroxy-7-methoxyindole: 1.0 g
- ethylene glycol monobutyl ether: 25.0 g
- triethanolamine: qs pH 8.5
- water: qs 100.0 g After rinsing with water and drying, an olive-green hue is obtained which can be used to counter ginger tones.

EXAMPLE 15

Hair containing 90% white hair is colored by applying the following composition for 25 minutes:
- 2,3-dimethyl-7-hydroxy-4-methoxyindole: 1.0 g
- ethylene glycol monobutyl ether: 25.0 g
- triethanolamine: qs pH 8.7
- water: qs 100.0 g After rinsing with water and drying a pearly beige-blond color is obtained which is reinforced with further applications.

EXAMPLE 16

Hair containing 90% white hair is impregnated with a composition (A) which follows:
Composition (A):
6-hydroxy-7-methoxyindole: 2.5 g
ethanol: 20.0 g
water: qs 100.0 g
The spontaneous pH is about 5.8.

The composition is kept in contact with the hair for 15 minutes, followed by rinsing with running water and draining.

A composition (B) is then applied which has the following composition:
Composition (B):
sodium nitrite: 2.5 g
hydrochloric acid qs pH=3
water: qs 100.0 g This composition is kept in contact with the hair for 9 minutes. The hair is then rinsed and washed with a shampoo containing 5% sodium lauryl sulphate. A highlight the color of which is dark coppery mahogany is thus obtained.

EXAMPLE 17

Dyeing is carried out in the same manner as in Example 16, using composition (A) which follows:
Composition (A):
4-hydroxy-5-ethoxyindole: 2.5 g
ethanol: 40.0 g
water: qs 100.0 g
spontaneous pH=6.

Composition (B) is the same as that used in Example 16.

In this manner a light golden chestnut color is obtained on the same hair.

EXAMPLE 18

Dyeing is carried out as in Example 16, but using as composition (A), the following composition:
Composition (A):
4-hydroxy-5-methoxyindole: 2.5 g
ethanol: 50.0 g
water: qs 100.0 g
spontaneous pH=6.

A light golden chestnut color is obtained on the hair.

EXAMPLE 19

Dyeing is carried out as in Example 16, but using the following composition (A):
Composition (A):
2,3-dimethyl-7-methoxy-4-hydroxyindole: 2.5 g
ethanol: 50.0 g
water: qs 100.0 g
spontaneous pH=6.
An orangish color is obtained on the hair.

EXAMPLE 20

Dyeing is carried out as in Example 16, but using the following composition (A):
Composition (A):
2,3-dimethyl-4-methoxy-7-hydroxyindole: 2.0 g
ethanol: 30.0 g
water: qs 100.0 g
spontaneous pH=5.8

An orangish yellow color is obtained on the hair.

EXAMPLE 21

The following tinctorial composition for hair is prepared:
5,6-dihydroxyindole: 0.5 g
4-hydroxy-5-methoxyindole: 0.2 g
ethyl alcohol: 10.0 g
xanthan gum sold under the name of Rhodopol by the Rhone-Poulenc company: 2.0 g
glycoside alkyl ether sold under the name Triton CG 110 by the Seppic company: 2.1 g AS
tartaric acid: 0.3 g
triethanolamine: 4.0 g
preservatives qs
demineralized water: qs 100.0 g This gel is applied on grey hair containing 90% white hair for 10 minutes.

After rinsing and drying a uniform pearl grey color is obtained which is reinforced on further applications.

EXAMPLE 22

The following tinctorial composition for hair is prepared:
Composition (A):
2,3-dimethyl-4-methoxy-7-hydroxyindole: 0.4 g
5,6-dihydroxyindole: 0.25 g
ethyl alcohol: 15.0 g
nonylphenol containing 9 moles of ethylene oxide sold under the name Cemulsol NP 9 by the Rhone-Poulenc company: 4.0 g
triethanolamine: qs pH 7
demineralized water: qs 100.0 g
Composition (B):
sodium periodate: 5.0 g
hydrochloric acid: qs pH 3
demineralized water: qs 100.0 g Composition (A) is applied on grey hair containing 90% white hair for 20 minutes.

After rinsing composition (B) is applied for 15 minutes. The hair is again rinsed and dried. The hair is then dyed in a golden ash-blond hue.

EXAMPLE 23

The following tinctorial composition for hair is prepared:
Composition (A):
6-hydroxy-7-methoxyindole: 0.25 g
5,6-dihydroxyindole: 0.15 g
sodium lauryl ether sulphate containing 2 moles of ethylene oxide sold under the name Sactipon 8533 by the Lever company: 3.0 g AS
ethylene glycol monobutyl ether: 8.0 g
triethanolamine qs pH 6.5
demineralized water: qs 100.0 g
Composition (B):
sodium periodate: 5.0 g
hydrochloric acid qs pH 3
demineralized water: qs 100.0 g Composition (A) is applied for 30 minutes on grey hair containing 90% white hair. The hair is rinsed and then composition (B) is applied for 15 minutes.

After rinsing again, the hair, which then has a dark blond color, is dried.

EXAMPLE 24

The following tinctorial composition for hair is prepared:

Composition (A):
4-hydroxy-5-methoxyindole: 0.3 g
3-methyl-5,6-dihydroxyindole: 0.5 g
5,6-dihydroxyindole: 0.3 g
ethyl alcohol: 10.0 g
guar gum sold under the name Jaguar HP 60 by the Celanese company: 1.0 g
glycoside alkyl ether sold under the name of Triton CG 110 by the Seppic company: 5.0 g AS
preservatives qs
pH adjusted to 6.7
demineralized water: qs 100.0 g
Composition (B):
sodium periodate: 5.0 g
hydrochloric acid qs pH 3
demineralized water: qs 100.0 g Composition (A) is applied on grey hair containing 90% white hair. After rinsing, at the end of 15 minutes, composition (B) is applied for 15 minutes. The hair is again rinsed and dried. The hair is colored a dark chestnut hue.

EXAMPLE 25

A gel for coloring the skin is prepared as follows:
4-hydroxy-5-ethoxyindole: 0.5 g
ethyl alcohol: 15.0 g
guar gum sold under the name Jaguar HP 60 by the Celanese company: 1.0 g AS
preservative: 0.6 g
triethanolamine qs pH 8.5
water: qs 100.0 g This gel is applied on the skin at a rate of 2 mg/cm². An immediate violet color of fairly great intensity is obtained, which does not develop 1 hour and 5 hours after application.

EXAMPLE 26

The following tinctorial composition for furs is prepared:
4-hydroxy-5-methoxyindole: 1.0 g
diethylene glycol monobutyl ether: 5.0 g
nonylphenol containing 9 moles of ethylene oxide sold under the name Sinnopal NP 9 by the Henkel company: 3.75 g
sodium lauryl ether sulphate containing 2 moles of ethylene oxide sold under the name Sactipon by the Lever company: 1.5 g AS
copra diethanolamide sold under the name of Comperlan KD by the Henkel company: 0.75 g
triethanolamine qs pH 4.2
demineralized water: qs 100.0 g
Hairs of the following animal species:
fox (white portion of the tail)
marmot (grey portion of the tail)
brown bison
are immersed in this composition for 15 minutes.

After rinsing, there hairs are immersed in a 20 volume solution of hydrogen peroxide at pH 3 for 3 minutes.

After rinsing and drying in air, the following colors are obtained:
fox: intense violet
marmot: smoked violet
bison: deep black.

I claim:

1. A process for dyeing a keratin material comprising applying to said keratin material an effective amount of a composition comprising in a medium suitable for dyeing said keratin material a dyestuff having the formula

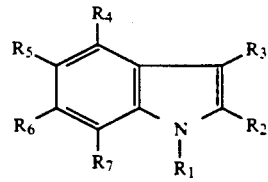

wherein
$R_1$ represent hydrogen, lower alkyl or $-SiR_{11}R_{12}R_{13}$,
$R_2$ and $R_3$, each independently, represent hydrogen, alkyl, carboxyl, lower alkoxy carbonyl or $-COO-SiR_{11}R_{12}R_{13}$,
$R_4$, $R_5$, $R_6$ and $R_7$, each independently represent hydrogen or O—Z wherein Z represents hydrogen, linear or branched $C_1$-$C_{20}$ alkyl, aralkyl, formyl, linear or branched $C_2$-$C_{12}$ acyl, linear or branched $C_3$-$C_{20}$ alkenyl, $-SiR_{11}R_{12}R_{13}$, $-P(O)(OR_8)_2$ or $R_8OSO_2-$,
the pairs $R_4$ and $R_5$, or $R_5$ and $R_6$, or $R_6$ and $R_7$, together with the carbon atoms to which each of said pairs are attached, being able to form a ring optionally containing a carbonyl group, a thiocarbonyl group, a $>P(O)(OR_8)$ group group or a $>CR_9R_{10}$ group group,
with the proviso that at least two of said $R_4$, $R_5$, $R_6$ and $R_7$ represent OZ or form a ring, and that at least one of $R_4$ or $R_7$ represents OZ,
$R_8$ and $R_9$ represent hydrogen or lower alkyl,
$R_{10}$ represents lower alkoxy, monoalkylamino or dialkylamino,
$R_{11}$, $R_{12}$ and $R_{13}$, each independently, represent linear or branched lower alkyl,
the alkali metal, alkaline earth metal, ammonium and amine salts thereof.

2. The process of claim 1 wherein said dyestuff of formula I is selected from the group consisting of
4-hydroxy-5-methoxyindole,
6-hydroxy-7-methoxyindole,
7-hydroxy-6-methoxyindole,
5-ethoxy-4-hydroxyindole,
5-ethoxy-4-hydroxy-1-methylindole,
7-ethoxy-6-hydroxyindole,
4-hydroxy-5-methoxy-2-methylindole,
6-hydroxy-7-methoxy-2-methylindole,
5-ethoxy-4-hydroxy-2-methylindole,
7-ethoxy-6-hydroxy-2-methylindole,
5,7-dimethoxy-6-hydroxyindole,
5,6,7-trihydroxyindole,
indole 4-hydroxy-5-methoxy-2-ethyl carboxylate,
indole 6-hydroxy-7-methoxy-2-ethyl carboxylate,
indole 7-hydroxy-6-methoxy-2-ethyl carboxylate,
indole 4-hydroxy-5-methoxy-2-carboxylic acid,
indole 6-hydroxy-7-methoxy-2-carboxylic acid,
indole 7-hydroxy-6-methoxy-2-carboxylic acid, indole 5,6,7-trihydroxy-2-carboxylic acid,
2,3-dimethyl-4-methoxy-7-hydroxyindole and
2,3-dimethyl-7-methoxy-4-hydroxyindole.

3. The process of claim 1 comprising, in a first stage, applying to said keratin material said composition containing said dyestuff of formula I and having a neutral or acid pH, permitting said composition to remain in contact with said keratin material for a period of time ranging from 5 to 60 minutes, draining said composition from said keratin material and optionally rinsing said keratin material, and in a second stage, contacting said keratin material with an agent to oxidize and develop said dyestuff of formula I.

4. The process of claim 3 where in said second stage, said keratin material is contacted with air whereby the oxygen of the air oxidizes and develops said dyestuff or with a peroxide or with a persalt, the oxidation of said dyestuff being catalyzed or uncatalyzed.

5. The process of claim 1 comprising applying to said keratin material said composition containing said dyestuff of formula I in an alkaline medium, permitting said composition to remain in contact with said keratin material for a period of time ranging from 5 to 60 minutes, rinsing said keratin material, optionally washing and rinsing said keratin material and drying said keratin material.

6. The process of claim 5 comprising superimposing a plurality of applications of said composition containing said dyestuff of formula I to said keratin material so as to effect a progressive dyeing of said keratin material.

7. The process of claim 1 comprising contacting said keratin material, either prior to or subsequent to the application of said composition containing said dyestuff of formula I, with a metal salt.

8. The process of claim 7 wherein said keratin material, subsequent to contact with said composition containing said dyestuff of formula I and an optional rinsing operation, is contacted with a hydrogen peroxide solution.

9. A process for dyeing a keratin material comprising applying to said keratin material a composition (A) comprising, in a medium suitable for dyeing said keratin material, at least one dyestuff having the formula

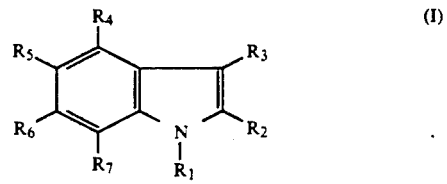

wherein
$R_1$ represent hydrogen, lower alkyl or $-SiR_{11}R_{12}R_{13}$,
$R_2$ and $R_3$, each independently, represent hydrogen, alkyl, carboxyl, lower alkoxy carbonyl or $-COO-SiR_{11}R_{12}R_{13}$,
$R_4$, $R_5$, $R_6$ and $R_7$, each independently represent hydrogen or O—Z wherein Z represents hydrogen, linear or branched $C_1$-$C_{20}$ alkyl, aralkyl, formyl, linear or branched $C_2$-$C_{12}$ acyl, linear or branched $C_3$-$C_{20}$ alkenyl, $-SiR_{11}R_{12}R_{13}$, $-P(O)(OR_8)_2$ or $R_8OSO_2-$,
the pairs $R_4$ and $R_5$, or $R_5$ and $R_6$, or $R_6$ and $R_7$, together with the carbon atoms to which each of said pairs are attached, being able to form a ring optionally containing a carbonyl group, a thiocarbonyl group, a $>P(O)(OR_8)$ group group or a $>CR_9R_{10}$ group group,
with the proviso that at least two of said $R_4$, $R_5$, $R_6$ and $R_7$ represent OZ or form a ring, and that at least one of $R_4$ or $R_7$ represents OZ,
$R_8$ and $R_9$ represent hydrogen or lower alkyl,
$R_{10}$ represents lower alkoxy, monoalkylamino or dialkylamino,
$R_{11}$, $R_{12}$ and $R_{13}$, each independently, represent linear or branched lower alkyl,
the alkali metal, alkaline earth metal, ammonium and amine salts thereof, and
a source of iodide ions,
the application of said composition (A) being preceded or followed by the application to said keratin material of a composition (B) comprising, in a medium suitable for dyeing said keratin material, hydrogen peroxide.

10. A process for dyeing a keratin material comprising applying to said keratin material a composition (A) comprising, in a medium suitable for dyeing said keratin material, at least one dyestuff having the formula

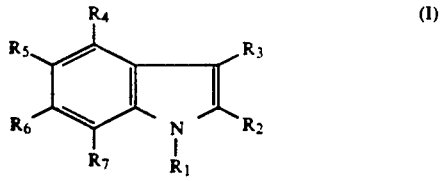

wherein
$R_1$ represent hydrogen, lower alkyl or $-SiR_{11}R_{12}R_{13}$,
$R_2$ and $R_3$, each independently, represent hydrogen, alkyl, carboxyl, lower alkoxy carbonyl or $-COO-SiR_{11}R_{12}R_{13}$,
$R_4$, $R_5$, $R_6$ and $R_7$, each independently represent hydrogen or O—Z wherein Z represents hydrogen, linear or branched $C_1$-$C_{20}$ alkyl, aralkyl, formyl, linear or branched $C_2$-$C_{12}$ acyl, linear or branched $C_3$-$C_{20}$ alkenyl, $-SiR_{11}R_{12}R_{13}$, $-P(O)(OR_8)_2$ or $R_8OSO_2-$,
the pairs $R_4$ and $R_5$, or $R_5$ and $R_6$, or $R_6$ and $R_7$, together with the carbon atoms to which each of said pairs are attached, being able to form a ring optionally containing a carbonyl group, a thiocarbonyl group, a $>P(O)(OR_8)$ group group or a $\diagup CR_9R_{10}$ group group,
with the proviso that at least two of said $R_4$, $R_5$, $R_6$ and $R_7$ represent OZ or form a ring, and that at least one of $R_4$ or $R_7$ represents OZ, $R_8$ and $R_9$ represent hydrogen or lower alkyl, $R_{10}$ represents lower alkoxy, monoalkylamino or dialkylamino, $R_{11}$, $R_{12}$ and $R_{13}$, each independently, represent linear or branched lower alkyl, the alkali metal, alkaline earth metal, ammonium and amine salts thereof, and a solution of hydrogen peroxide having a pH ranging from 2 to 7, the application of said composition (A) being preceded or followed by the application to said keratin material of a composition (B) comprising, in a medium suitable for dyeing said keratin material, a source of iodide ions.

11. A process for dyeing a keratin materiarl comprising applying to said keratin material a composition (A) comprising, in a medium suitable for dyeing said keratin material, at least one dyestuff having the formula

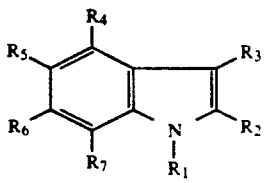

(I)

wherein
$R_1$ represent hydrogen, lower alkyl or —$SiR_{11}R_{12}R_{13}$, $R_2$ and $R_3$, each independently, represent hydrogen, alkyl, carboxyl, lower alkoxy carbonyl or —COO-$SiR_{11}R_{12}R_{13}$, $R_4$, $R_5$, $R_6$ and $R_7$, each independently represent hydrogen or O—Z wherein Z represents hydrogen, linear or branched $C_1$-$C_{20}$ alkyl, aralkyl, formyl, linear or branched $C_2$-$C_{12}$ acyl, linear or branched $C_3$-$C_{20}$ alkenyl, —$SiR_{11}R_{12}R_{13}$, —P(O)-$(OR_8)_2$ or $R_8OSO_2$—, the pairs $R_4$ and $R_5$, or $R_5$ and $R_6$, or $R_6$ and $R_7$, together with the carbon atoms to which each of said pairs are attached, being able to form a ring optionally containing a carbonyl group, a thiocarbonyl group, a $\diagup P(O)(OR_8)$ group group or a $\diagup CR_9R_{10}$ group group,
with the proviso that at least two of said $R_4$, $R_5$, $R_6$ and $R_7$ represent OZ or form a ring, and that at least one of $R_4$ or $R_7$ represents OZ, $R_8$ and $R_9$ represent hydrogen or lower alkyl, $R_{10}$ represents lower alkoxy, monoalkylamino or dialkylamino, $R_{11}$, $R_{12}$ and $R_{13}$, each independently, represent linear or branched lower alkyl, the alkali metal, alkaline earth metal, ammonium and amine salts thereof, the application of said composition (A) to said keratin material being followed by the application to said keratin material of a composition (B) comprising an aqueous composition having an acid pH, said composition (A) or (B) also containing at least one nitrite.

12. A process for dyeing a keratin material comprising, in a first stage, applying to said keratin material a composition comprising, in a medium suitable for dyeing said keratin material, an anion of metal having good affinity for keratini and having an oxidoreduction potential greater than that of a compound of formula I, defined below, and in a second stage, applying to said keratin material a composition comprising, in a medium suitable for dyeing said keratin material, at least one dyestuff having the formula

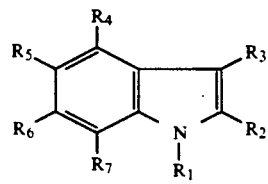

(I)

wherein
$R_1$ represent hydrogen, lower alkyl or —$SiR_{11}R_{12}R_{13}$, $R_2$ and $R_3$, each independently, represent hydrogen, alkyl, carboxyl, lower alkoxy carbonyl or —COO-$SiR_{11}R_{12}R_{13}$, $R_4$, $R_5$, $R_6$ and $R_7$, each independently represent hydrogen or O—Z wherein Z represents hydrogen, linear or branched $C_1$-$C_{20}$ alkyl, aralkyl, formyl, linear or branched $C_2$-$C_{12}$ acyl, linear or branched $C_3$-$C_{20}$ alkenyl, —$SiR_{11}R_{12}R_{13}$, —P(O)-$(OR_8)_2$ or $R_8OSO_2$—, the pairs $R_4$ and $R_5$, or $R_5$ and $R_6$, or $R_6$ and $R_7$, together with the carbon atoms to which each of said pairs are attached, being able to form a ring optionally containing a carbonyl group, a thiocarbonyl group, a $\diagup P(O)(OR_8)$ group group or a $\diagup CR_9R_{10}$ group group,
with the proviso that at least two of said $R_4$, $R_5$, $R_6$ and $R_7$ represent OZ or form a ring, and that at least one of $R_4$ or $R_7$ represents OZ, $R_8$ and $R_9$ represent hydrogen or lower alkyl, $R_{10}$ represents lower alkoxy, monoalkylamino or dialkylamino, $R_{11}$, $R_{12}$ and $R_{13}$, each independently, represent linear or branched lower alkyl, the alkali metal, alkaline earth metal, ammonium and amine salts thereof.

13. The process of claim 12 wherein said anion is a permanganate or bichromate anion.

14. A composition for dyeing a keratin material comprising, in a medium suitable for dyeing said keratin material, at least one dyestuff having the formula

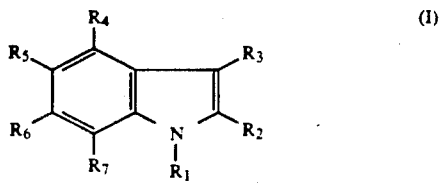

(I)

wherein
$R_1$ represent hydrogen, lower alkyl or $-SiR_{11}R_{12}R_{13}$,
$R_2$ and $R_3$, each independently, represent hydrogen, alkyl, carboxyl, lower alkoxy carbonyl or $-COOSiR_{11}R_{12}R_{13}$,
$R_4$, $R_5$, $R_6$ and $R_7$, each independently represent hydrogen or O—Z wherein Z represents hydrogen, linear or branched $C_1$-$C_{20}$ alkyl, aralkyl, formyl, linear or branched $C_2$-$C_{12}$ acyl, linear or branched $C_3$-$C_{20}$ alkenyl, $-SiR_{11}R_{12}R_{13}$, $-P(O)(OR_8)_2$ or $R_8OSO_2-$,
the pairs $R_4$ and $R_5$, or $R_5$ and $R_6$, or $R_6$ and $R_7$, together with the carbon atoms to which each of said pairs are attached, being able to form a ring optionally containing a carbonyl group, a thiocarbonyl group, a $>P(O)(OR_8)$ group group or a $>CR_9R_{10}$ group group,
with the proviso that at least two of said $R_4$, $R_5$, $R_6$ and $R_7$ represent OZ or form a ring, and that at least one of $R_4$ or $R_7$ represents OZ,
$R_8$ and $R_9$ represent hydrogen or lower alkyl,
$R_{10}$ represents lower alkoxy, monoalkylamino or dialkylamino,
$R_{11}$, $R_{12}$ and $R_{13}$, each independently, represent linear or branched lower alkyl,
the alkali metal, alkaline earth metal, ammonium and amine salts thereof.

15. The compositioin of claim 14 wherein said dyestuff of formula I is present in an amount ranging from 0.01 to 5 percent by weight based on the total weight of said composition.

16. The compositioin of claim 14 wherein said dyestuff of formula I is present in an amount ranging from 0.03 to 2.5 percent by weight based on the total weight of said composition.

17. The compositioin of claim 14 in the form of a thickened or unthickened liquid, a cream, a foam, a gel, an oil or a powder to be diluted with a liquid at the time of use.

18. The compositioin of claim 14 wherein said medium suitable for dyeing said keratin material is essentially an aqueous medium having a pH ranging from 3.5 to 11.

19. The compositioin of claim 14 wherein said medium suitable for dyeing said keratin material is essentially an aqueous medium having a pH ranging from 5 to 10.5.

20. The compositioin of claim 14 wherein said medium suitable for dyeing said keratin material comprises a solvent selected from the group consisting of a lower $C_1$-$C_4$-alkanol, ethylene glycol, propylene glycol, monomethylether of ethylene glycol, monoethylether of ethylene glycol, monobutylether of etylene glycol, ethylene glycol monoethylether acetate, monomethylethersof propylene glycol, monomethylether of dipropylene glycol and methyl lactate.

21. The composition of claim 20 wherein said solvent is present in an amount ranging from 1 to 60 percent by weight based on the total weight of said composition.

22. The composition of claim 20 wherein said solvent is present in an amount ranging from 3 to 30 percent by weight based on the total weight of said composition.

23. The composition of claim 20 wherein said medium suitable for drying said keratin material is essentially anhydrous and consists of said solvent.

24. The composition of claim 14 which also includes a surfactant present in an amount ranging from 0.1 to 50 percent by weight based on the total weight of said composition.

25. The composition of claim 14 which also includes a surfactant present in an amount ranging from 1 to 40 percent by weight based on the total weight of said composition.

26. The composition of claim 14 which also contains an anionic, non-ionic, cationic or amphoteric polymer or a mixture thereof; a thickener; a penetration agent; a swelling agent; a sequestering agent; an antioxidant; a buffer; an electrolyte; or a fragrance.

27. The composition of claim 14 which also includes 5,6-dihydroxyindole.

28. The composition of claim 14 which also contains another colorant selected from the group consisting of an oxidation dyestuff and a direct dyestuff.

29. The composition of claim 14 which also contains iodide ions.

30. The composition of claim 14 which also contains a nitrite.

* * * * *